United States Patent [19]

Krepski et al.

[11] Patent Number: 4,694,103

[45] Date of Patent: Sep. 15, 1987

[54] METHOD OF PREPARING N-ACRYLOYL-α-AMINO ACIDS

[75] Inventors: Larry R. Krepski, White Bear Lake; Howell K. Smith, II, Lauderdale; Jerald K. Rasmussen, Stillwater; Steven M. Heilmann, N. St. Paul, all of Minn.

[73] Assignee: Minnesota Mining and Manufacturing Company, St. Paul, Minn.

[21] Appl. No.: 865,190

[22] Filed: May 19, 1986

[51] Int. Cl.$^4$ .............................................. C07C 99/10
[52] U.S. Cl. .................................... 562/450; 558/346; 558/351; 558/426; 558/445; 562/574; 562/503; 562/505; 562/507; 546/330; 546/335
[58] Field of Search ............... 562/450, 403, 505, 507, 562/574; 558/346, 351, 426, 445; 540/330, 335

[56] References Cited

U.S. PATENT DOCUMENTS

| | | | |
|---|---|---|---|
| 2,587,043 | 2/1952 | Hawkins | 558/445 |
| 2,675,383 | 4/1954 | de Benneville | 558/346 |
| 3,275,677 | 9/1966 | Allen et al. | 558/346 |
| 3,285,886 | 11/1966 | Gunderson et al. | 260/80.3 |
| 3,396,030 | 8/1968 | Haas | 96/114 |
| 3,615,624 | 10/1971 | Smith et al. | 96/114 |
| 3,713,834 | 1/1973 | Fitzgerald | 96/114 |
| 3,932,168 | 1/1976 | Stein et al. | 558/426 |
| 3,966,789 | 6/1976 | Oishi et al. | 558/445 |
| 4,157,418 | 6/1979 | Heilmann | 428/355 |
| 4,164,511 | 8/1979 | Distler et al. | 558/445 |
| 4,273,934 | 10/1979 | Heilmann | 526/298 |
| 4,304,705 | 12/1981 | Heilmann et al. | 260/30.4 |
| 4,335,256 | 1/1982 | de Witt et al. | 558/450 |
| 4,378,411 | 3/1983 | Heilmann et al. | 428/500 |
| 4,451,619 | 5/1984 | Heilmann et al. | 525/379 |

FOREIGN PATENT DOCUMENTS 1425423 4/1973 United Kingdom .

OTHER PUBLICATIONS

D. V. Ioffe et al., J. Gen. Chem. USSR, 29, 3766 (1959).
B. U. Kaczmar, et al., Chem. Abstr. 85, 124738w (1976).
T. Uemura et al., Chem. Abstr. 69, 19709 (1968).
T. Yamashita et al., Bull. Chem. Soc., Japan, 43, 1809, (1970).
Y. Ihara et al., J. Polymer Sco, Polymer Che. Ed., 10, 3569, (1972).
G. Blaschke, et al., Chem. Abstr., 85, 75405k (1976).
E. Masuhara et al., Chem. Abstr., 68 5045a (1968).
Y. Kozai et al., Chem. Abstr., 75, 50182e (1971).
U. Einsele, et al., Chem. Abstr., 81, 79204y, (1974).
A. Winston et al., J. Polymer Sci., Polymer Chem. Ed. 13, 2019 (1975).
K. Huebner, et al., Angew, Makromol. Chem. 11, 109 (1970).
Morrison et al., Organic Chemistry, Allyn & Bacon Inc., pp. 588–589 (1966).

*Primary Examiner*—James H. Reamer
*Attorney, Agent, or Firm*—Donald M. Sell; James A. Smith; Lorraine R. Sherman

[57] ABSTRACT

A novel, one-pot procedure for the preparation of N-acryloyl-α-amino acids involves the steps of:
(i) reacting a ketone, an ammonium salt, and a cyanide salt in water, optionally in the presence of ammonium hydroxide and a co-solvent, to form an aminonitrile;
(ii) acryloylating the aminonitrile in aqueous media to afford an acrylamidonitrile; and
(iii) hydrolyzing with aqueous acid the acrylamidonitrile to provide the N-acryloyl-α-amino acid.

15 Claims, No Drawings

METHOD OF PREPARING N-ACRYLOYL-α-AMINO ACIDS

Field of the Invention

This invention relates to a novel process for the preparation of N-acryloyl-α-amino acids which are useful as monomers and synthetic intermediates.

Background of the Invention

N-Acryloyl-α-amino acids are useful free radical addition monomers. U.S. Patent Nos. 4,157,418 and 4,172,934 disclose pressure-sensitive adhesives and tapes possessing substantially increased performance by inclusion of N-acryloyl-α-amino acid comonomers.

Copolymers derived from N-acryloyl-α-amino acids are reknowned for their ability to undergo ion exchange reactions and for their chelating ability. D. V. Ioffe, et al., *J. Gen. Chem. USSR*, 29, 3766 (1959) disclose N-methacryloylglycine:ethylene dimethacrylate copolymers as cation exchange resins; U.S. Pat. No. 3,285,886 discloses N-acryloylglycine:acrylic acid copolymers as agents for control of boiler sludge, corrosion inhibition, industrial waste treatment, and for desalination; so-called "snake cage" polymers were prepared by B. U. Kaczmar, et al., *Chem. Abstr.*, 85, 124738w (1976) which possess both anionic and cationic exchange ability.

Column chromatography supports derived from these monomers are disclosed by T. Uemura, et al., *Chem. Abstr.*, 69, 19709j (1968); by T. Yamashita, et al., *Bull. Chem. Soc. (Japan)*, 43, 1809 (1970); by Y. Ihara, et al., *J. Polymer Sci.: Polymer Chem. Ed.*, 10, 3569 (1972); and by G. B-laschke, et al., *Chem. Abstr.*, 85, 78405k (1976).

Polymers derived from N-acryloyl-α-amino acids are useful replacements for gelatin in photographic emulsions (see, for example, U.S. Pat. Nos. 3,396,030; 3,615,624; and 3,713,834); the monomers also find use as components in photopolymerizable photographic formulations (GB 1,425,423).

The monomers have been utilized as priming systems on teeth (E. Masuhara, et al., *Chem. Abstr.*, 68, 50454a (1968)) and as grafting monomers! to increase the hydrophilicity of natural rubber (Y. Kozai, et al., *Chem. Abstr.*, 75, 50182e (1971)) and the soil release c.haracteristics of cotton (U. Einsele, et al., *Chem. Abstr.*, 81, 79204y (1974)).

In addition to their implementation as free radical monomers, N-acryloyl-α-amino acids have often been transformed into other useful monomers. Esterification with N-hydroxysuccinimide yields a monomer which contains a readily displaceable group; this principle was utilized by A. Winston, et al., *J. Polymer Sci.: Polymer Chem. Ed.*, 13, 2019 (1975) in preparing an iron (III) complexing polymer.

Perhaps the most common transformation of an N-acryloyl-α-amino acid, however, is into its corresponding 2-vinyl azlactone via a cyclodehydration reaction:

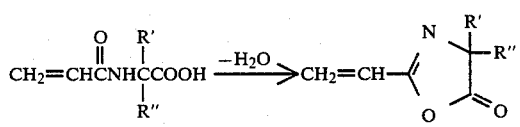

Vinyl azlactones have been utilized as monomers for generating reactive polymers in, for example, U.S. Pat. Nos. 4,304,705, 4,378,411, and 4,451,619.

The essential ingredient in all of the above-mentioned technologies, either directly or indirectly, is the N-acryloyl-α-amino acid. N-Acryloyl-α-amino acids have traditionally and, prior to the instant invention, most expediently been prepared by acryloylation of an alkali metal salt of an amino acid in water using acryloyl chloride (see, for example, U.S. Pat. No. 4,157,418 for a detailed procedure). There are at least two disadvantages with this method of synthesis: (1) the method requires that the corresponding amino acid be available, which is not always the case, especially with α,α-disubstituted amino acids useful in vinyl azlactone syntheses and, in addition, conventional procedures for preparing common amino acids often give low yields and require tedious isolation procedures involving formation of toxic heavy metal or pyridinium salts in the work-up procedure; and (2) yields employing this procedure are often low and quite variable, e.g., 20–80% reported by K. Huebner, et al., *Angew. Makromol. Chem.*, 11, 109 (1970).

SUMMARY OF THE INVENTION

Briefly, the present invention provides a novel process for preparing N-acryloyl-α-amino acids. The method involves transformation of a readily available ketone via a series of chemical reactions into the corresponding N-acryloyl-α-amino acid in one reaction vessel (one-pot procedure). The reaction proceeds without isolation of intermediates, in high yield, and in aqueous media, from which the product, in all but a few instances, crystallizes and can be isolated by filtration.

The novel, one-pot procedure for the preparation of N-acryloyl-α-amino acids involves the steps of:

(i) reacting a ketone having alkyl, aryl, or arenyl groups or a combination of these groups with an ammonimum salt and a cyanide salt, in water, optionally in the presence of ammonium hydroxide and a co-solvent, to form an aminonitrile;

(ii) acryloylating the resulting aminonitrile in aqueous media to afford an acrylamidonitrile; and (iii) hydrolyzing with aqueous acid the resulting acrylamidonitrile to provide the N-acryloyl-α-amino acid.

In this application:

"alkyl" means the monovalent residue remaining after removal of a hydrogen atom from a linear or branched chain hydrocarbon having 1 to 14 carbon atoms;

"aryl" means the monovalent residue remaining after removal of one hydrogen atom from an aromatic or heteroaromatic compound which can consist of one ring or two fused or catenated rings having 5 to 12 ring atoms which can include up to 3 heteroatoms selected from S, N, and O. The carbon atoms can be substituted by up to three halogen atoms, $C_1$–$C_4$ alkyl, $C_1$–$C_4$ alkoxy, N,N-di($C_1$–$C_4$ alkyl)amino, nitro, cyano, $C_1$–$C_4$ alkyl carboxylic ester, and sulfonyl groups;

"arenyl" means the monovalent residue remaining after removal of a hydrogen atom from the alkyl portion of a hydrocarbon containing both alkyl and aryl groups having 6 to 26 carbon and heteroatoms (wherein the heteroatoms are up to 3 S, N, and O atoms); and "acryloyl" means not only 1-oxo-2-propenyl but also 1-oxo-2-methyl-2-propenyl resulting from methacryloylation reactions.

DETAILED DESCRIPTION OF THE INVENTION

The present invention provides a process for preparing N-acryloyl-α-amino acids having the formula:

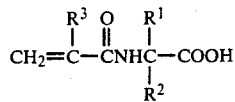

wherein
$R^1$ and $R^2$ independently can be an alkyl group having 1 to 14 carbon atoms, a cycloalkyl group having 3 to 14 carbon atoms, an aryl group having 5 to 12 ring atoms, an arenyl group having 6 to 26 carbon and heteroatoms, or $R^1$ and $R^2$ taken together with the carbon to which they are joined can form a carbocyclic ring containing 4 to 12 ring atoms, with the proviso that only one of $R^1$ and $R^2$ can be aryl, and $R^3$ can be hydrogen or methyl, the process comprising the steps which take place in a single vessel without isolation of the intermediate products as follows:

(i) reacting an alkyl, aryl or arenyl (or combinations thereof) ketone having 3 to 53 carbon and heteroatoms (which can include up to 7 N, S, and O heteroatoms, e.g., in the case of a diarenyl ketone), an ammonium salt, and an alkali metal cyanide, in water, to provide an aminonitrile, (ii) acryloylating the aminonitrile to provide an acrylamidonitrile, and (iii) hydrolyzing the acrylamidonitrile in aqueous acid to provide the N-acryloyl-α-amino acid.

The novel process for preparation of these N-acryloyl-α-amino acids uses a ketone as starting material and preferably takes place in aqueous media, in a stepwise manner using one reaction vessel, and in a fashion whereby the product can be isolated in high yield from the reaction mixture by filtration. The process is depicted in the flow chart below;

FLOW CHART

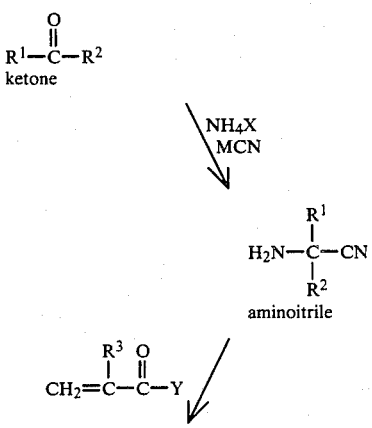

-continued
FLOW CHART

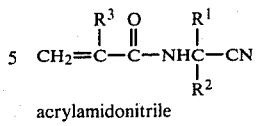
acrylamidonitrile

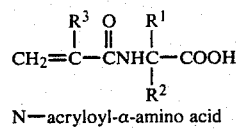
N—acryloyl-α-amino acid wherein
$R^1$, $R^2$, and $R^3$ are as defined above,
X can be chloride, bromide, nitrate, or sulfate, and
Y can be chloro or acryloyloxy.
The steps of the process are as follows:

STEP 1

This step involves transformation of a readily available ketone into the corresponding aminonitrile

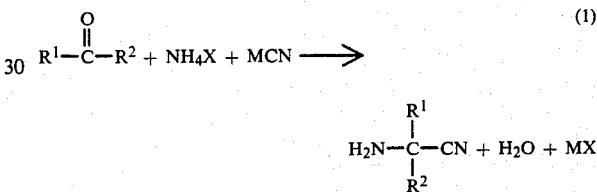

wherein:
$R^1$ and $R^2$ can be as defined above,
X can be chloride, bromide, nitrate, or sulfate, and
M can be sodium, potassium, or lithium.

The reaction can be conducted by adding a fairly concentrated aqueous solution, i.e., 5–15 M, of the cyanide reagent to a mixture of an aqueous solution, i.e., 1–10 M ammonium salt and preferably a modest stoichiometric excess, i.e., 1–50 mole percent, of the ketone (i.e., ketone to cyanide reagent preferably being 1:1 to 1.5:1). Relatively concentrated aqueous solutions can be employed in this early stage not only to increase the rate of the reaction in equation (1) but also to keep at a minimum the amount of water, from which the eventual, somewhat water-soluble N-acryloyl-α-amino acid desirably will crystallize. Use of a slight stoichiometric excess of the ketone facilitates the rate of reaction of equation (1) without being deleterious to future steps in the novel process; this procedure also results in less residual toxic cyanide. The reaction requires efficient agitation, especially with those ketones that are only sparingly soluble in water; temperatures from 10°–80° C., preferably 20°–30° C.; and reaction times of 1 to 24 hours, preferably 1 to 16 hours. Progress of the reaction can conveniently be monitored by gas liquid chromatography or various spectroscopic techniques such as NMR and IR.

In certain instances when the ketone is essentially insoluble in water, non-reactive, water miscible, organic co-solvents such as ethanol, isopropanol, N,N-dimethylformamide, dioxane, and N,N-dimethylacetamide may be added in sufficient amount to create a medium for reaction to occur. Also, in other certain instances (e.g., with conjugated ketones such as aryl substituted ketones) when the aminonitrile is difficult to form under the above reaction conditions, it may be necessary to add ammonia to the system, generally in the form of aqueous ammonium hydroxide. Furthermore, the excess ammonia apparently stabilizes the aminonitrile product from dimerizing as depicted in equation (2). Such dimerization reactions are disclosed in U.S. Pat. No. 4,543,215.

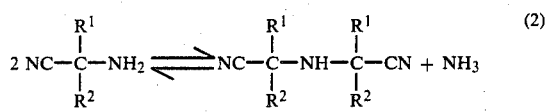
(2)

Preferred ketone starting materials include but are not limited to acetone, 2-butanone 3-pentanone, cyclopentanone, cyclohexanone, cycloheptanone, acetophenone, propiophenone, 4'-methoxyacetophenone, 3'-chloroacetophenone, and dibenzyl ketone. The preferred ammonium salt is ammonium chloride, and the preferred cyanide salts are either sodium or potassium cyanide Aminonitriles are well-known compounds, being prepared from the corresponding aldehyde or ketone by treatment with ammonium chloride and sodium cyanide in aqueous medium; this reaction is known as the Zelinsky-Stadnikoff modification of the Strecker Amino Acid Synthesis (cf. a review by D. T. Mowry, *Chem. Rev.*, 42, 231-240 (1948)). A further modification of introducing ammonium hydroxide (exemplified in U.S. Pat. No. 3,803,208) is sometimes employed to facilitate formation of the aminonitrile and to further stabilize it from dimer formation.

STEP 2

The second step in the novel process involves acryloylation of the aminonitrile to form the corresponding acrylamidonitrile, depicted in equation (3).

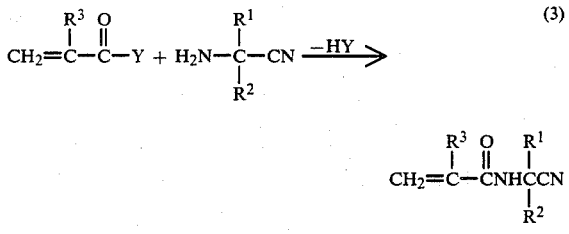
(3)

wherein $R^1$, $R^2$, and $R^3$ are as defined above, and

Y can be chloro or (meth)acryloyloxy.

The preferred acryloylating agents are acryloyl and methacryloyl chloride. Both are liquids at room temperature, i.e., 22°-25° C., and can be conveniently added without solvent to the aqueous mixture containing the aminonitrile of STEP 1, with the proviso that when excess ammonia has been added in the special cases described in STEP 1 that the ammonia be removed at reduced pressure prior to the addition of the acryloylating agent. In most instances only the water solvent and efficient stirring are necessary even though the (meth)acryloyl chloride reagent is essentially insoluble in water. This is because the acryloylation reaction is believed to take place at the interface between the (meth)acryloyl chloride and the aqueous solution of the aminonitrile, and the aminonitrile compounds are generally more water-soluble than their ketone precursors. However, in a few instances use of a co-solvent such as those described in STEP 1 is necessary to bring the aminonitrile into a reactive environment.

As is depicted in equation (3) above, acid in the form of HY is generated during the reaction which will react with and render unreactive the instantaneous excess of the aminonitrile. Although two equivalents of the aminonitrile can be utilized, this procedure is wasteful of the necessary aminonitrile reactant and is undesirable. We have found an attractive alternative is to add sodium or potassium hydroxide to the reaction mixture to react with the generated acid. Most conveniently, a stoichiometric equivalent of sodium or potassium hydroxide is dissolved in a volume of water equivalent to the volume of the (meth)acryloyl chloride. The aqueous base can then be added independently and concomitantly at the same rate as the (meth)acryloyl chloride reagent by simple visual inspection. Approximately equal addition rates of both reagents are desirable so that the pH of the reaction mixture does not vary substantially; when the pH is too low the reaction rate is depressed, and when too high the possibility of polymerization and other side reactions becomes more probable.

The temperature of the addition reaction is very important. If the temperature of the reaction mixture exceeds about 15° C., hydrolysis of the (meth)acryloyl chloride, i.e., reaction with water, rather than the desired acryloylation of the aminonitrile becomes significant. Useful reaction temperatures for STEP 2 are from 0°-15° C., preferably 5°-10° C. After the additions, the reaction mixture is stirred for an additional 0.5 to 2 hours to ensure complete reaction of all the (meth)acryloyl chloride; again, progress of the reaction can be monitored by gas chromatography and/or spectral techniques.

Aminonitriles have been N-acylated using acryloyl and methacryloyl chloride in U.S. Pat. No. 2,744,943, but only in a non-aqueous medium, i.e., using benzene, employing two equivalents of aminonitrile, the extra equivalent of aminonitrile being utilized to react with the hydrogen chloride generated in the acylation reaction. No yields were given, and the resulting (meth)acrylamidonitriles were not converted to N-acryloyl-α-amino acids by hydrolysis but were isolated by tedious extraction procedures and were further reacted with dicyandiamide to form (meth)acrylamidoacylguanamines. Other N-acyl-α-aminonitrile compounds have been prepared and hydrolyzed, but again only by the process of first isolating the aminonitrile and then acylating in an organic solvent. Roesler, et al., (*Chem Abstr.*, 66, 115427z (1967)) reported that cyclic structures resulting from intramolecular attack on the nitrile function by the carbonyl group were formed when N-aryl-N-acyl substituted aminonitriles were treated with strong acids, e.g., hydrogen chloride, trifluoroacetic acid, or chlorosulfonic acid. That cyclic structures were formed in acid-catalyzed reactions of N-acyl-α-aminonitriles was also supported by a later report by Poupaert, et al., *Synthesis*, 622 (1972). Shirai, et al., *Yuki Gosei Kagaku Kyoaki Shi*, 30, 76 (1972) studied both the acid- and base-catalyzed hydrolyses of certain N-acyl-αaminonitriles and they observed competitive hydrolysis between the acyl and nitrile functions.

STEP 3

This step in the novel process involves the selective hydrolysis of the acrylamidonitrile to the N-acryloyl-α-amino acids of the invention. This reaction is depicted in equation (4).

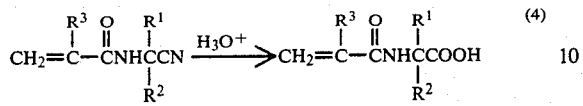

wherein:

$R^1, R^2$, and $R^3$ are as defined above. Surprisingly, the hydrolysis reaction depicted above can only be effected with aqueous acid. In contrast to the report by Shirai, et al., *Yuki Gosei Kagaku Kyokai Shi*, 30, 76 (1972) which indicated that either aqueous acid or base was effective in hydrolyzing n-alkanoylaminonitriles, we have unexpectedly discovered that aqueous base does not lead to the desired hydrolysis products with N-acryloyl-α-aminonitriles. In no instance was any N-acryloyl-α-amino acid product isolated when the selective hydrolysis was attempted using an aqueous hydroxide reagent such as sodium hydroxide. With aqueous acid, however, the desired N-acryloyl-α-amino acids are readily formed, generally crystallize in the reaction mixture, and can be isolated in essentially pure form in chemical yields of 50% or higher by simple filtration.

Useful aqueous acids include hydrochloric, sulfuric, phosphoric, and nitric acids, with sulfuric acid being preferred. (Hydrochloric acid works well but its addition to the reaction mixture often causes co-precipitation of sodium chloride with the N-acryloyl-α-amino acid product because of the common ion effect. Removal of the sodium chloride is in many instances nontrivial because of the appreciable water solubility of some of the N-acryloyl-α-amino acids.) Useful hydrolysis temperatures are 25°–90° C., preferably 25°–60° C., and useful times of 3–24 hours.

The N-acryloyl-α-amino acids are colorless, crystalline solids having melting points that vary according to the ketones used in their preparation. Isolation of the N-acryloyl-α-amino acids occurs most frequently and desirably by simple filtration of the crystalline product. In instances when the product does not crystallize, it may be isolated by extracting into a substantially water-insoluble organic solvent such as ethyl acetate and purifying by conventional methods such as recrystallization or chromatography.

In certain instances, it has been discovered that the isolated N-acryloylamino acid product is contaminated with the β-chloropropionyl derivative, i.e., the HCl addition product. This can conveniently be dehydrochlorinated to the N-acryloylamino acid product by dissolution in dilute aqueous sodium hydroxide, followed by reacidification.

Representative examples of N-acryloyl-α-amino acids which can be prepared by the process of the instant invention include compounds of the formula

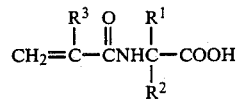

wherein $R^1$, $R^2$, and $R^3$ can be as shown in TABLE I below:

TABLE I

| $R^1$ | $R^2$ | $R^3$ |
|---|---|---|
| —CH₃ | —CH₃ | —H |
| —CH₃ | —CH₃ | —CH₃ |
| —CH₃ | —C₂H₅ | —H |
| —CH₃ | —C₆H₅ | —H |
| —(CH₂)₃CH₃ | —(CH₂)₃CH₃ | —H |
| —(CH₂)₄CH₃ | —(CH₂)₄CH₃ | —H |
| —C₂H₅ | —C₂H₅ | —H |
| —CH₂C₆H₅ | —CH₂C₆H₅ | —H |
| —(CH₂)₅CH₃ | —(CH₂)₅CH₃ | —CH₃ |
| —CH₃ | m-C₆H₄Cl | —H |
| —C₂H₅ | —C₆H₅ | —CH₃ |
| —CH₃ | p-C₆H₄OCH₃ | —H |
| —C₁₂H₂₅ | —CH₃ | —H |
| —CH₃ | 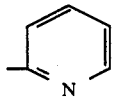 | —CH₃ |
| —(CH₂)₃— | | —H |
| —(CH₂)₄— | | —CH₃ |
| —(CH₂)₅— | | —H |
| —(CH₂)₆— | | —CH₃ |
| —(CH₂)₇— | | —H |

N-Acryloyl-α-amino acids, as noted in the Background of the Invention above, are useful as monomers and as synthetic intermediates. In particular, they are useful in providing 2-vinyl azlactones. The resulting vinyl azlactones are exceedingly interesting and useful compounds whose ultimate potential has not yet been fully realized. They have been utilized as reactive co-monomers for purposes of covalently attaching various modifying groups to the side chains of polymers. This procedure has been utilized to prepare radiation-sensitive polymers (U.S. Pat. Nos. 4,304,705 and 4,378,411), hydrophilic/hydrophobic polymers (U.S. Pat. No. 4,451,619), and pressure sensitive adhesives (Eur. Pat. Appl. Publications No. 0128731 (1984). By reaction with appropriate nucleophiles, the vinyl azlactones have themselves been transformed into other monomers useful in the photographic arts (U.S. Pat. No. 4,288,523); into azlactone-functional compounds useful as monomers, chain extending agents, and curing agents for step-growth polymers (U.S. Pat. No. 4,485,236); and into acrylamide-functional compounds useful in curable coatings, adhesives, and binders (Int. Publication No.: WO83/01617 (1983)).

Having described our invention in general terms, it is now further described by specific examples of preparations of various N-acryloyl-α-amino acids by utilization of our novel process. The particular materials and amounts recited in the examples, however, as well as other details and conditions, should not be construed to unduly limit the invention.

EXAMPLE 1

Preparation of N-Acryloylmethylalanine

A one-liter Morton flask equipped with a mechanical stirrer, thermometer, and two addition funnels was charged with acetone (1.1 moles), ammonium chloride (53.5 grams; 1 mole), and deionized water (200 mL). A freshly prepared solution of sodium cyanide (49 grams; 1 mole) in deionized water (100 mL) was added such that the reaction temperature does not exceed 10° C. The mixture was then allowed to warm to room temperature and was stirred briskly for one hour. With efficient cooling, i.e., dry ice/isopropanol bath, acryloyl chloride (81.45 grams, 73 mL, 0.90 mole) and a caustic solution [36 grams (0.90 mole) of sodium hydroxide in 75 mL of water] were added dropwise from the addition funnels such that the temperature did not exceed 10° C. After the addition, the mixture was stirred without cooling for 30 minutes. Concentrated hydrochloric acid (250 mL; 3.02 moles) was added, and the resulting mixture warmed to 70° C. for 3 hours. After cooling to room temperature, the crystalline product was isolated by filtration and washed with 250 mL of cold water. The N-acryloylmethylalanine product weighed 95.3 grams and exhibited an acid equivalent weight of 176 (assay=89%; chemical yield=60%); the solid may be further purified, if desired, by recrystallization from acetonitrile or ethyl acetate. The compound exhibited satisfactory spectral and elemental analyses.

EXAMPLE 2

This Example teaches that purer product can be obtained by use of sulfuric acid as hydrolyzing acid instead of hydrochloric acid. When the procedure of Example 1 was conducted using sulfuric acid (12.1 N, 3.02 equivalents), a crystalline solid was obtained possessing an acid equivalent weight of 161 (assay=97.5%; chemical yield=58%). Furthermore, when sulfuric acid (24 N, 3.02 equivalents) was utilized, a crystalline product was obtained with an equivalent weight of 165 (assay=95%; chemical yield=60%).

EXAMPLE 3

Preparation of N-Acryloylethylalanine

The procedure of Example 1 was utilized except that the reaction time for the initial aminonitrile-forming step was extended to 16 hours, and the hydrolysis condition was 60° C. for three hours. The chemical yield of N-acryloylethylalanine obtained was 73% by filtering the crystalline material obtained after the hydrolysis step.

EXAMPLE 4

Preparation of N-Methacryloylmethylalanine

Using the procedure of Example 1, methacryloyl chloride (94 g; 0.90 mole) was substituted for acryloyl chloride. After hydrolysis with 12.1N HCl, the filtered solid weighed 105 g and had an equivalent weight of 234 (73% assay; chemical yield=50%).

EXAMPLE 5

Preparation of 1-Acrylamidocyclohexanecarboxylic Acid

Using the procedure of Example 3 the initially filtered crystalline product weighed 180 grams and possessed an equivalent weight of 265 (74% assay). When this impure product was washed with cold water (300 mL), a solid weighing 126.3 grams possessing the theoretical equivalent weight of 197 was obtained; this represents a chemical yield of 1-acrylamidocyclohexanecarboxylic acid of 71%.

EXAMPLE 6

Preparation of 1-Acrylamidocyclopentanecarboxylic Acid

Using the procedure of Example 2, except that the aminonitrile-forming step was extended to 21 hours, hydrolysis with 12N sulfuric acid produced 81.7 g of a white solid possessing an equivalent weight of 182 (assay 91%; chemical yield=50%).

EXAMPLE 7

Preparation of 2-Acrylamido-2-ethylbutyric Acid

This Example teaches use of an organic solvent to extract the N-acryloylamino acid product from the reaction mixture. Using the procedure of Example 2 and a hydrolysis condition of sulfuric acid (24 N) for 16 hours at room temperature, no crystalline product was formed as had been observed in all other cases. The yellow aqueous reaction mixture was extracted with ethyl acetate (500 mL). After drying over anhydrous magnesium sulfate, removal of the ethyl acetate at reduced pressure left 84 grams of a light brown oil which solidified on standing. Filtration and recrystallization from acetonitrile produced 63.6 grams of a white crystalline solid melting at 141°–142° C.; chemical yield=38%.

EXAMPLE 8

Preparation of 2-Acrylamido-2-phenylpropanoic Acid

This Examples teaches the use of a cosolvent in Steps 1 and 2 and the use of ammonium hydroxide solution in Step 1.

A three-liter Morton flask equipped with a mechanical stirrer, thermometer, and condenser was charged with acetophenone (1.05 moles), ammonium chloride (59 grams, 1.1 moles), sodium cyanide (49 grams, 1.0 mole), deionized water (240 mL), ammonium hydroxide solution (15.1M) (270 mL), and ethanol (400 mL). The solution was stirred and heated at 60° C. for 5 hours, then left at room temperature overnight. The solution was then concentrated to a volume of 300–400 mL on a rotary evaporator. The reaction flask was then equipped with a mechanical stirrer, thermometer, and two addition funnels. After the addition of ethanol (250 mL), the flask was cooled in an ice bath and acryloyl chloride (81.5 grams, 73 mL, 0.90 mole) and a caustic solution [36 grams 0.90 mol) of sodium hydroxide in 40 mL of water] were added dropwise from the addition funnels at such a rate that the temperature of the vigorously stirred reaction mixture did not exceed 10° C. After the addition, the mixture was stirred without cooling for 2 hours, water (500 mL) was added, and the mixture was filtered. The solid from the filtration was suspended in a solution of sulfuric acid (18 M) (160 mL) in water (400 mL) and the mixture was warmed to 60° C. After 4 hours, the reaction mixture was cooled to room temperature and filtered. After washing with water (500 mL), the collected solid was slurried in 500 mL of a mixture of ether and hexane (40:60, volume:volume). Filtration afforded 71.1 grams of 2-acrylamido-2-phenylpropionic acid as a white solid possessing an acid equivalent weight of 229 (assay=96%; chemical yield=33%).

EXAMPLE 9

Preparation of 1-Acrylamidocycloheptanecarboxylic Acid.

This example teaches the dehydrochlorination of 1-β-chloropropionamido)cycloheptane carboxylic acid.

Using the procedure of Example 6, 113.1 g of a white solid was obtained. Analysis by nuclear magnetic resonance spectroscopy determined the material to consist mainly of 1-acrylamidocycloheptanecarboxylic acid, together with about 10% of the HCl addition product, 1-(β—chloropropionamido)cycloheptane carboxylic acid. The mixture was dissolved in a sodium hydroxide solution (40 g in 400 mL of water), stirred at room temperature for 3 hours, then concentrated sulfuric acid (60 mL) was added. The white solid was collected by filtration, washed with water (500 mL), and dried to afford 101.5 g of 1-acrylamidocycloheptane-carboxylic acid (assay=98%; chemical yield=48%).

Various modifications and alterations of this invention will become apparent to those skilled in the art without departing from the scope and spirit of this invention, and it should be understood that this invention is not to be unduly limited to the illustrative embodiments set forth herein.

We claim:

1. A process for providing an N-acryloyl-α-amino acid comprising the steps:
    (i) reacting a ketone having alkyl, aryl, or arenyl groups, or combinations of these groups, said ketone having 3 to 53 carbon and heteroatoms which can include up to 7 N, S, and O heteroatoms, an ammonium salt, and an alkali metal cyanide, in water, to provide an aminonitrile,
    (ii) acryloylating the resulting aminonitrile with an acryloylating agent having the formula,

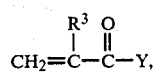

wherein $R^3$ is hydrogen or methyl and Y is chloride, methacryloyloxy, or acryloyloxy, in aqueous media to provide an acrylaminodonitrile, and
    (iii) hydrolyzing the resulting acrylamidonitrile in aqueous acid to provide said N-acryloyl-α-amino acid.

2. A process for providing an N-acryloyl-α-amino acid having the formula

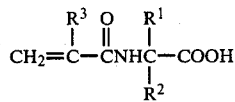

wherein:
$R^1$ and $R^2$ are independently an alkyl group of 1 to 14 carbon atoms, a cycloalkyl group of 3 to 14 carbon atoms, an aryl group of 5 to 12 ring atoms, an arenyl group of 6 to 26 carbon and heteroatoms, or $R^1$ and $R^2$ taken together with the carbon to which they are joined form a carbocyclic ring containing 4 to 12 ring atoms, with the proviso that only one of $R^1$ and $R^2$ can be aryl, and
$R^3$ is hydrogen or methyl, said process comprising the steps:
    (i) reacting a ketone of the formula

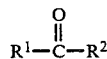

with ammonium salt, $NH_4X$, and a metal cyanide, MCN, in water, to provide an aminonitrile, wherein $R^1$ and $R^2$ are as previously defined, X is chloride, bromide, nitrate, or sulfate, and M is sodium, potassium, or lithium,
    (ii) acryloylating the resulting aminonitrile with an acryloylating agent having the formula,

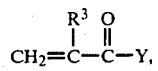

wherein $R^3$ is as previously defined and Y is chloride, methacryloyloxy, or acryloyloxy, to provide an acrylamidonitrile, and
    (iii) hydrolyzing the resulting acrylamidonitrile in aqueous acid to provide said N-acryloyl-α-amino acid.

3. The process according to claim 2 wherein the step of reacting said ketone, an ammonium salt, and metal cyanide further comprises as reactants ammonium hydroxide and a non-reactive, water miscible, organic co-solvent.

4. The process according to step 3 wherein said co-solvent is ethanol, isopropanol, N,N-dimethylformamide, dioxane, or N,N-dimethylacetamide.

5. The process according to claim 2 wherein said reaction takes place in one vessel without isolation of intermediate compounds.

6. The process according to claim 2 wherein said ratio of ketone to metal cyanide is in the range of 1:1 to 1.5:1.

7. The process according to claim 2 wherein step (i) takes place at a temperature in the range of 10° to 80° C.

8. The process according to claim 2 wherein the acryloylation reaction of step (ii) takes place in the presence of sodium or potassium hydroxide.

9. The process according to claim 2 wherein step (ii) takes place at a temperature in the range of 0° to 15° C.

10. The process according to claim 2 wherein the aqueous acid of step (iii) is hydrochloric, sulfuric, phosphoric, or nitric acid.

11. The process according to claim 2 wherein said N-aryloyl-α-amino acid is formed in a yield of 50 percent or higher.

12. The process according to claim 2 wherein said N-acryloyl-α-amino acid is
    N-acryloylmethylalanine,
    N-acryloylethylalanine,
    N-methacryloylmethylalanine,
    1-acrylamidocyclopentanecarboxylic acid,
    1-acrylamidocyclohexanecarboxylic acid,
    1-acrylamidocycloheptanecarboxylic acid,
    2-acrylamido-2-ethylbutyric acid, and
    2-acrylamido-2-phenylpropanoic acid.

13. The process according to claim 2 wherein said N-acryloyl-α-amino acid is isolated from the reaction mixture with a substantially water-insoluble organic solvent.

14. The process according to claim 13 wherein said organic solvent is ethyl acetate.

15. The process according to claim 2 wherein said N-acryloyl-α-amino acid is isolated by filtration.

* * * * *

UNITED STATES PATENT AND TRADEMARK OFFICE
CERTIFICATE OF CORRECTION

PATENT NO. : 4,694,103
DATED : September 15, 1987
INVENTOR(S) : Larry R. Krepski et al It is certified that error appears in the above-identified patent and that said Letters Patent is hereby corrected as shown below:

Column 12, line 21, "step" should read -- claim --.

Signed and Sealed this

Thirteenth Day of September, 1988

Attest:

DONALD J. QUIGG

*Attesting Officer*

*Commissioner of Patents and Trademarks*